(12) United States Patent
Segletes et al.

(10) Patent No.: US 8,823,369 B2
(45) Date of Patent: Sep. 2, 2014

(54) MULTI DIRECTIONAL ELECTROMAGNETIC YOKE FOR INSPECTION OF BORES

(75) Inventors: David S. Segletes, York, SC (US); Erik A. Lombardo, Sharon, SC (US)

(73) Assignee: Siemens Energy, Inc., Orlando, FL (US)

( * ) Notice: Subject to any disclaimer, the term of this patent is extended or adjusted under 35 U.S.C. 154(b) by 431 days.

(21) Appl. No.: 13/109,183

(22) Filed: May 17, 2011

(65) Prior Publication Data

US 2012/0293168 A1 Nov. 22, 2012

(51) Int. Cl.
*G01N 27/72* (2006.01)
*G01N 27/82* (2006.01)
*G01R 33/12* (2006.01)
*G01N 27/84* (2006.01)

(52) U.S. Cl.
CPC .............. *G01N 27/84* (2013.01); *G01N 27/72* (2013.01); *G01N 27/82* (2013.01); *G01R 33/12* (2013.01)
USPC ........... 324/220; 324/221; 324/237; 324/238; 324/240; 324/228; 324/243; 324/216; 324/529; 702/34; 702/38; 702/35; 336/221; 336/222; 336/225

(58) Field of Classification Search
CPC ............... H01F 5/02; H01F 5/04; H01F 5/06; G01N 27/72; G01N 27/82; G01N 27/84; G01R 33/12
USPC ................ 324/220, 221, 228–243, 216, 529; 702/34, 38, 35; 336/221, 222, 225
See application file for complete search history.

(56) References Cited

U.S. PATENT DOCUMENTS

| | | | | |
|---|---|---|---|---|
| 3,553,672 | A * | 1/1971 | 340/627 | |
| 3,573,979 | A * | 4/1971 | Honjo | 427/127 |
| 3,855,530 | A | 12/1974 | Fuji et al. | |
| 3,932,827 | A * | 1/1976 | Buhrer | 336/60 |
| 5,633,583 | A * | 5/1997 | Podney | 324/241 |
| 6,462,535 | B1 * | 10/2002 | Schwabe | 324/164 |
| 2001/0017540 | A1 * | 8/2001 | Arai | 324/236 |
| 2002/0039062 | A1 * | 4/2002 | Kvarnsjo et al. | 336/221 |
| 2005/0253957 | A1 * | 11/2005 | Gustavsson et al. | 348/363 |
| 2006/0151142 | A1 * | 7/2006 | Schoen et al. | 164/476 |
| 2006/0164080 | A1 * | 7/2006 | Popovic et al. | 324/244 |
| 2008/0150669 | A1 * | 6/2008 | Kawai | 336/222 |
| 2008/0288183 | A1 * | 11/2008 | Potdar et al. | 702/34 |
| 2009/0050043 | A1 * | 2/2009 | Alvarez | 114/197 |
| 2009/0242200 | A1 * | 10/2009 | Badoux et al. | 166/255.2 |
| 2009/0302836 | A1 * | 12/2009 | De Smet | 324/242 |
| 2010/0301851 | A1 * | 12/2010 | Park et al. | 324/240 |

FOREIGN PATENT DOCUMENTS

| | | |
|---|---|---|
| DE | 4034751 A1 | 5/1991 |
| DE | 4215168 A1 | 5/1992 |
| DE | 102004054127 A1 | 5/2006 |
| EP | 0645787 A1 | 3/1995 |
| SE | 3709143 A1 | 9/1988 |

* cited by examiner

*Primary Examiner* — Patrick Assouad
*Assistant Examiner* — Lamarr Brown

(57) ABSTRACT

A non-destructive inspection system that has particular application for inspecting a bore in a valve for defects. The system includes an inspection yoke having a ferromagnetic core, where a first coil is wound around the core in one direction and a second coil is wound around the core in an orthogonal direction so that orthogonal electromagnetic fields can be generated within the bore. A controller provides a current flow through the coils to generate the electromagnetic fields to detect defects in the bore.

20 Claims, 1 Drawing Sheet

MULTI DIRECTIONAL ELECTROMAGNETIC YOKE FOR INSPECTION OF BORES

BACKGROUND OF THE INVENTION

1. Field of the Invention

This invention relates generally to an inspection device that generates an electromagnetic field for inspecting a bore and, more particularly, to a non-destructive testing system including an inspection device having orthogonal windings that provide multidirectional electromagnetic fields for inspecting bores in large valves for defects.

2. Discussion of the Related Art

Steam turbines are large machines that include many interconnected parts for converting thermal energy from steam to rotational energy to perform work. Some of these parts are large valves having bores that control fluid flow at various locations in the turbine in a manner that is understood by those skilled in the art. Because the valves operate in a very harsh thermal environment, the valve bores typically need to be periodically inspected for wear, defects and other discontinuities, such as surface induced cracks, that could detrimentally affect the operation of the turbine. Therefore, it is known in the art to periodically remove the valves and other components from the turbine and perform various maintenance procedures, such as during machine refurbishing, in a laboratory environment to inspect the valve bores for such defects.

Non-destructive testing of valve bores using a magnetic particle inspection process and electromagnetic fields during maintenance procedures is known in the art. In one know inspection process, an elongated cable or rod is inserted into the bore of the valve, where the rod includes a coil that is able to carry a current flow. The rod is generally inserted down the center of the bore to evenly provide the electromagnetic field over the entire circumference of the bore. The current flow in the coil generates an electromagnetic field around the coil that interacts with the ferroelectric valve structure through which the bore passes. The electromagnetic field causes currents to be induced in the valve structure proximate the bore, and if a discontinuity exists in the bore, the current and associated magnetic field cause a magnetic hysteresis loss at the discontinuity, which attracts iron or other magnetic particles. The valve body would typically be electrically coupled to a grounding line to allow the current flow in the valve structure. A solution including a suitable dye and suspended magnetic particles is provided on the internal surface of the bore. If a discontinuity exists, the magnetic particles collect at the discontinuity as a result of the hysteresis loss, which becomes more visible as a result of the higher intensity of the dye at those locations. Cameras, optical detectors, mirrors, etc. can be strategically placed relative to the bore so that this visual indication of a discontinuity can be observed by the technician performing the inspection.

The above described non-destructive test has limitations because of its ability to provide a suitable electromagnetic field strength in the valve structure that is necessary for generating the desired magnetic hysteresis loss at the discontinuities. Particularly, because the bores in many of these valves are quite large, the distance between the inspection device and the bore wall can be significant, where the field strength generated by the coil in the device drops off considerably before interacting with the valve structure. Making the inspection device larger in diameter has various drawbacks, including the need for having multiple inspection devices of different sizes, the increased size and weight of the inspection device, etc. Therefore, for many larger bores, the ability to detect certain defects or discontinuities is limited and sometimes not possible.

Further, the inspection device for the known testing system of this type includes a single coil that provides an electromagnetic field in a single direction relative to the bore. Particularly, the winding direction of the coil provides an electromagnetic field that induces a current flow in the valve structure in a direction along the length of the bore. For those defects that are perpendicular to this direction, the current would cause the magnetic particles to readily collect at the defect. However, for those defects that are parallel to the direction of the bore, where the direction of the current flow would be substantially parallel to the defect, the current flow would be limited in its ability to cause magnetic particles to collect at the defect.

SUMMARY OF THE INVENTION

In accordance with the teachings of the present invention, a non-destructive inspection system is disclosed that has particular application for inspecting a bore in a valve for defects. The system includes an inspection yoke having a ferromagnetic core, where a first coil is wound around the core in one direction and a second coil is wound around the core in an orthogonal direction so that orthogonal electromagnetic fields can be generated within the bore. A controller provides a current flow through the coils to generate the electromagnetic fields to detect defects in the bore.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a non-destructive inspection system is merely exemplary in nature, and is in no way intended to limit the invention or its applications or uses. For example, the discussion herein is specifically directed to an inspection system for detecting discontinuities in a bore of a valve, where the valve is part of a steam turbine. However, as well be appreciated by those skilled in the art, the inspection system of the invention will have application for detecting defects in any bore provided in a conductive material that is operable to generate electrical currents therein from induced electromagnetic fields.

Figure 1:
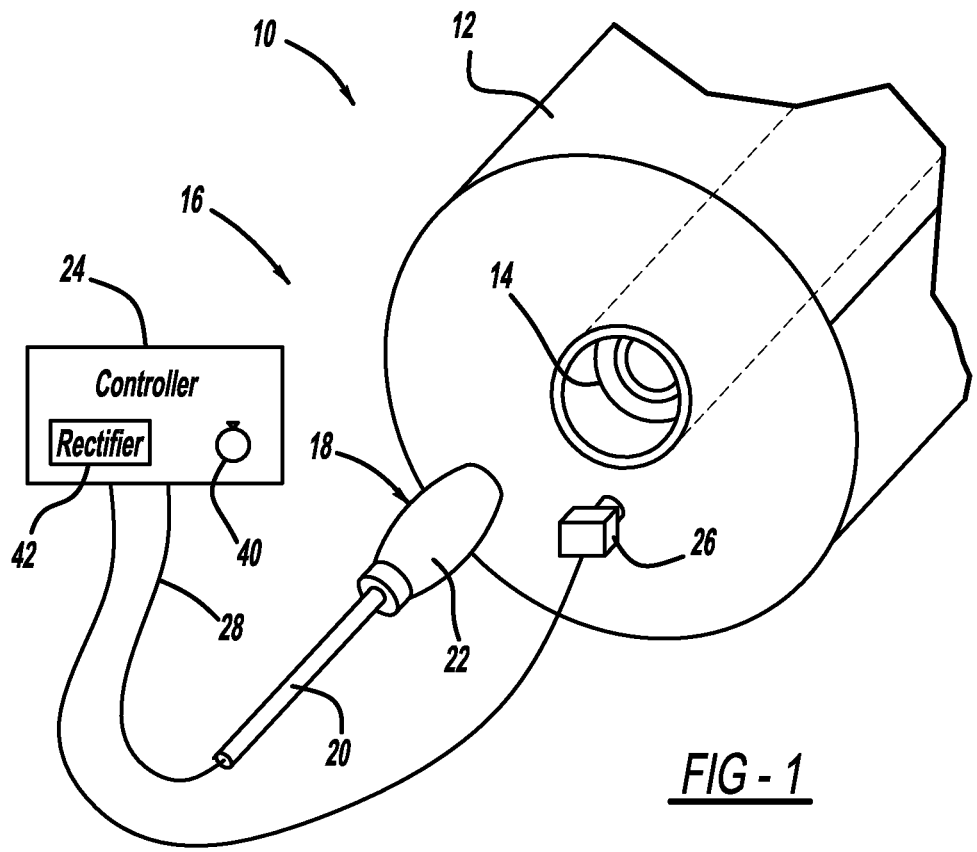
FIG. 1 is a plan view of a non-destructive inspection system for detecting discontinuities in a bore of a component.

FIG. 1 is an illustration of a testing environment 10 for non-destructively inspecting a component structure 12, such as a valve body of a valve, having a bore 14 extending therethrough using a non-destructive inspection system 16. The inspection system 16 includes an inspection device 18 mounted to an elongated member 20 that allows the device 18 to be inserted into the bore 14 for testing purposes consistent with the discussion herein. The device 18 can be manually inserted into the bore 14, or some suitable fixture (not shown)

can be provided to controllably insert the device 18 into the bore 14 so that it extends down a center of the bore 14.

As will be discussed in detail below, the inspection device 18 includes two orthogonally wound coils wrapped around a core and encased within a suitable protective material, such as a layer 22 of an epoxy resin or other potting material. A controller 24 provides a current flow to the windings in the inspection device 18 to generate electromagnetic fields to provide the inspection. A line 28 connects the testing device 18 to the controller 24, and is intended to represent the wiring necessary to provide the current flow to the coils within the device 18. A suitable optical device, such as a camera 26, can optically detect emissions from the bore 14 in response to the electromagnetic fields interacting with the component structure 12, which can be provided to the controller 24 to be displayed or can be visually observed at the bore 14. The camera 26 is intended to represent any suitable optical device or system that has application for the inspection system 16 discussed herein, many of which are well known to those skilled in the art.

Figure 2:
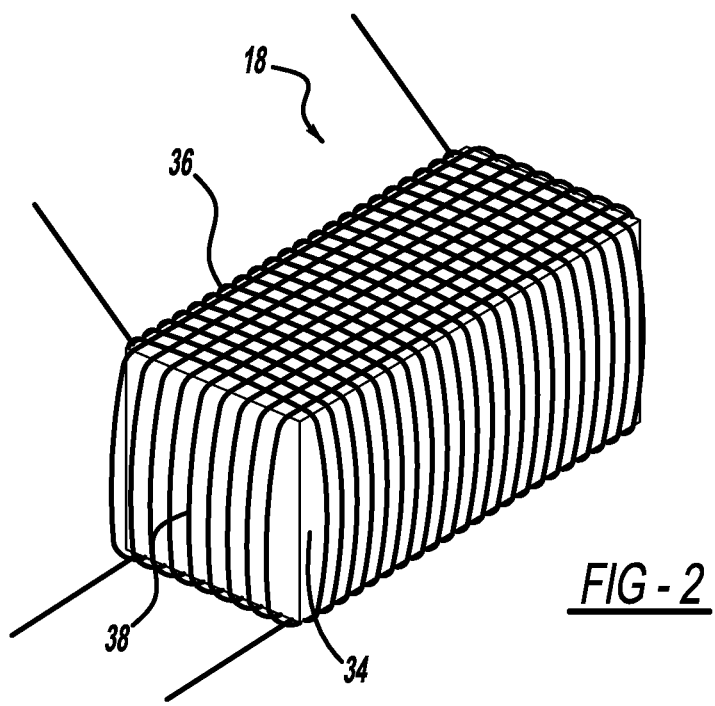
FIG. 2 is a perspective view of an inspection device associated with the inspection system shown in FIG. 1 and showing multiple windings.

FIG. 2 is a perspective view of the inspection device 18 with the outer protective layer 22 removed. The device 18 includes a core 34 made of a ferromagnetic material operable to increase the field strength of electromagnetic fields. The core 34 can be made of any suitable permeable magnetic material, such as iron. In one embodiment, the core 34 is a coated, non-oriented, high silicon electrical steel, although other materials may also be equally applicable. In this embodiment, the core 34 is block shaped having hard edges, although in other embodiment the core 34 may have other shapes. A first coil 36 is wound around the core 34 in one direction and a second coil 38 is wound around the core 34 in an opposite direction perpendicular to the coil 36, as shown.

The ferromagnetic core 34 increases the field strength of the electromagnetic field generated by the coils 36 and 38. For example, for a core having about a six inch diameter, the electromagnetic field extending from the core 34 can be increased by about ten times. The controller 24 provides and controls the current flow through the coils 36 and 38 and provides the power to generate the current. The controller 24 includes a switch 40 that selectively switches the current flow through the coils 36 and 38 on and off. When the current is flowing through the coil 36, the electromagnetic field generates a current in the structure 12 in a direction along the length of the bore 14, which is better suited to detect defects transverse to the bore 14. When the current flow is switched to the coil 38, the electromagnetic field generates a current in the structure 12 a direction lateral relative to the bore 14 that is better suited to detect defects in a longitudinal direction relative to the length of the bore 14.

Further, the controller 24 is able to generate both alternating current (AC) signals and direct current (DC) signals to the coils 36 and 38. In this embodiment, the controller 24 includes a rectifier circuit 42 that converts AC to DC, and can selectively provide either the AC signal or the DC signal to the coils 36 and 38 as desired. AC signals are more conducive for detecting surface defects within the bore 14 and DC signals are more conducive for detecting defects that are deeper in the structure 12. Further, the controller 24 can selectively control the power that provides the current flow through the coils 36 and 38, which also controls how deep the electromagnetic field can penetrate into the structure 12 and be more suitable for larger sized bores 14.

A technician will coat the inside of the bore 14 with a suitable solution having a colored dye and magnetic particles, such as iron particles, suspended therein. The technician will manually, or otherwise, insert the inspection device 18 into the bore 14 in a controlled manner at an appropriate speed and/or to a desired location in the bore 14 so that the currents induced in the structure 12 by the electromagnetic fields cause magnetic particles in the solution to collect at the discontinuity and be observed or recorded by the camera 26 while one of the coils 36 or 38 is activated. The same process can then be repeated with the other coil 36 or 38 activated.

The foregoing discussion disclosed and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. An inspection system for detecting defects in a bore of a component, said system comprising:
   an inspection device configured to be inserted into the bore, said inspection device including a core made of a ferromagnetic material, a first coil wound around the core in a first direction and a second coil wound around the core in a second direction, where the first and second directions are orthogonal to each other;
   a protective material that encases the core, the first coil and the second coil; and
   a controller programmed to control the inspection device, said controller selectively providing a current flow in the first coil and the second coil when the inspection device is within the bore to generate electromagnetic fields in orthogonal directions within the bore to detect the defects therein, wherein the current flow is selectively provided to detect surface defects and deep structure defects in directions that are transverse and longitudinal relative to the bore.

2. The system according to claim 1 wherein the ferromagnetic core is made of a non-oriented high silicon electrical steel.

3. The system according to claim 1 wherein the core has a general square cross-section.

4. The system according to claim 1 further comprising an optical device for detecting optical signals from the bore.

5. The system according to claim 4 wherein the optical device includes a camera.

6. The system according to claim 4 wherein the optical device detects colored magnetic particles.

7. The system according to claim 1 wherein the inspection device further includes an elongated member attached to the core that allows the inspection device to be manually inserted into the bore.

8. The system according to claim 1 wherein the controller is programmed to generate an alternating current signal or a direct current signal in the first and second coils.

9. The system according to claim 1 wherein the component is a valve.

10. The system according to claim 9 wherein the valve is a valve for a steam turbine.

11. An inspection system for detecting defects in a bore of a valve, said system comprising:
    an inspection device configured to be inserted into the bore, said inspection device including a core made of a ferromagnetic material, a first coil wound around a core in a first direction and a second coil wound around the core in a second direction, where the first and second directions are orthogonal to each other;
    an optical device for receiving optical signals from the bore; and a controller programmed to control the inspection device, said controller selectively providing a current flow in the first coil and the second coil when the inspection device is within the bore, where the first and second coils generate electromagnetic fields in orthogonal directions within the bore, and where the electromagnetic fields induce current in the valve that generates visual signals detectable by the optical device, wherein the current flow is selectively provided to detect surface defects and deep structure defects in directions that are transverse and longitudinal relative to the bore.

12. The system according to claim 11 wherein the ferromagnetic core is made of a non-oriented high silicon electrical steel.

13. The system according to claim 11 wherein the core has a general square cross-section.

14. The system according to claim 11 wherein the optical device detects colored magnetic particles.

15. The system according to claim 11 wherein the inspection device further includes an elongated member attached to the core that allows the inspection device to be inserted into the bore.

16. The system according to claim 11 wherein the controller is programmed to generate an alternating current signal or a direct current signal in the first and second coils.

17. The system according to claim 11 wherein the valve is a valve for a steam turbine.

18. An inspection device for detecting defects in a bore of a component, said device comprising a core, a first coil wound around the core in a first direction and a second coil wound around the core in a second direction, where the first and second directions are orthogonal to each other
   a protective material that encases the core, the first coil and the second coil; and
   a controller programmed to control the inspection device, said controller selectively providing a current flow in the first coil and the second coil when the inspection device is within the bore to generate electromagnetic fields in orthogonal directions within the bore to detect the defects therein, wherein the current flow is selectively provided to detect surface defects and deep structure defects in directions that are transverse and longitudinal relative to the bore.

19. The device according to claim 18 wherein the core is made of a ferromagnetic material.

20. The device according to claim 18 wherein the core has a general square cross-section.

\* \* \* \* \*